US012612345B1

(12) United States Patent
Bhasin et al.

(10) Patent No.: US 12,612,345 B1
(45) Date of Patent: Apr. 28, 2026

(54) CATALYSTS AND PROCESSES FOR OXIDATIVE DEHYDROGENATION OF METHANE AND ETHANE TO PRODUCE ETHYLENE, ETHANE, PROPANE, PROPYLENE, AND OTHER PRODUCTS

(71) Applicant: Innovative Catalytic Solutions, LLC, Charleston, WV (US)

(72) Inventors: Madan Mohan Bhasin, Charleston, WV (US); David A. Berry, Mount Morris, PA (US)

( * ) Notice: Subject to any disclaimer, the term of this patent is extended or adjusted under 35 U.S.C. 154(b) by 0 days.

(21) Appl. No.: 19/223,090

(22) Filed: May 30, 2025

Related U.S. Application Data

(60) Provisional application No. 63/809,440, filed on May 21, 2025.

(51) Int. Cl.
| | |
|---|---|
| C07C 5/48 | (2006.01) |
| B01J 23/34 | (2006.01) |
| B01J 35/00 | (2024.01) |
| B01J 37/02 | (2006.01) |
| C07C 11/04 | (2006.01) |

(52) U.S. Cl.
CPC ................. *C07C 5/48* (2013.01); *B01J 23/34* (2013.01); *B01J 35/00* (2013.01); *B01J 37/0201* (2013.01); *C07C 11/04* (2013.01); *C07C 2523/04* (2013.01); *C07C 2523/10* (2013.01); *C07C 2523/30* (2013.01); *C07C 2523/34* (2013.01)

(58) Field of Classification Search
None
See application file for complete search history.

(56) References Cited

U.S. PATENT DOCUMENTS

| | | | |
|---|---|---|---|
| 4,788,372 | A | 11/1988 | Gaffney |
| 4,795,849 | A | 1/1989 | Gaffney et al. |
| 6,403,526 | B1 | 6/2002 | Cantrell et al. |
| 6,576,803 | B2 | 6/2003 | Cantrell et al. |

(Continued)

OTHER PUBLICATIONS

Keller and Bhasin, "Synthesis of Ethylene via Oxidative Coupling of Methane", Journal of Catalysis vol. 73, pp. 9-19 (1982) USA.

(Continued)

*Primary Examiner* — Colin W. Slifka
(74) *Attorney, Agent, or Firm* — Jaensson Law , PLLC; Monika Jenson, Esq.

(57) ABSTRACT

A catalyst for the oxidative dehydrogenation of methane and/or ethane including manganese in the form of an oxide, mixed oxide, hydroxide, carbonate, oxycarbonate and/or a salt, and in embodiments further including tungsten, one or more alkali metals in the form of an oxide, mixed oxide, hydroxide, carbonate, oxycarbonate and/or a salt, and optionally a rare earth metal oxide, which when used for the oxidative dehydrogenation of the lower hydrocarbon at a pressure $\geq 5$ atm, and employing GHSV$\geq 1,000$ h$^{-1}$, has: a conversion of $\geq 10\%$ into at least one higher hydrocarbon, and a selectivity for $C_2$ and/or $C_3$ of $\geq 40\%$, for $\geq 15$ days. Further, a catalytic process for the oxidative dehydrogenation of methane and/or ethane, the process occurring in the presence of such a catalyst, operating at such pressures, temperatures, and GHSV, producing such conversion and selectivity for $\geq 15$ days, thereby resulting in yields $\geq 20\%$.

10 Claims, 7 Drawing Sheets

(56)                References Cited

U.S. PATENT DOCUMENTS 9,040,762 B2      5/2015   Cizeron et al.
2004/0034266 A1*   2/2004   Brophy ................ B01J 19/0093
                                                    422/198

OTHER PUBLICATIONS

Pinabiau-Carlier, et al., "The Effect of Total Pressure on the Oxidative Coupling of Methane Reaction under Cofeed Conditions", Natural Gas Conversion, pp. 183-190 (1991) USA.

Ekstrom, et al., "Effect of Pressure on the Oxidative Coupling Reaction of Methane," Applied Catalysis, vol. 62, pp. 253-269 (1990) USA.

Bhasin, et al., "Oxidative Coupling of Methane—A Progress Report", Methane and Alkane Conversion Chemistry, Plenum Press, NY, 1995 (USA).

Yu, et al., "High-pressure oxidative coupling of methane on alkali metal catalyst—Microkinetic analysis and operando thermal visualization", J. Catalysts, 432 (2024) 115414 (USA).

Yu, et al. "Mn—Na2WO4/SiO2-Tridymite with improved stability and selectivity for high-pressure oxidative coupling of methane", Chemical Engineering Journal, 500 (2024) 156938 (USA).

Godini, et al., Oxidative Coupling of Methane, Chapter 5 in Natural Gas Conversion to Value Added Chemicals, CRC Press, 2021, Edited by J. Hu and D. Shekhawat. (USA).

Kim, et al., "Reaction engineering of oxidative coupling of methane. Experimental observations and analysis of the impacts of operating parameters.", Chemical Engineering Research and Design, vol. 172, (2021) pp. 84-98 (USA).

Serres, et al., "Influence of the composition/texture of Mn—Na—W catalysts on the oxidative coupling of methane", Applied Catalysis A: General 504 (2015) 509-518 (USA).

Liu, et al. "Effect of pressure on oxidative coupling of methane over MgO/BaC03 catalyst—studies of its deativation at elevated pressure", Applied Catalysis A: General 168 (1998) 139-149 (USA).

Chen, et al. "Effect of Pressure on the Oxidative Coupling of Methane in the Absence of Catalyst", American Institute of Chemical Engineers Journal, vol. 40, No. 3, pp. 521-535 (Mar. 1994), USA.

* cited by examiner

CATALYSTS AND PROCESSES FOR OXIDATIVE DEHYDROGENATION OF METHANE AND ETHANE TO PRODUCE ETHYLENE, ETHANE, PROPANE, PROPYLENE, AND OTHER PRODUCTS

FIELD OF THE INVENTION

The disclosed technology regards novel catalyst compositions stable at pressures ≥about 5 atm, ≥about 10 atm, or ≥about 20 atm, and temperatures ≤about 700° C., ≤about 650° C., ≤about 600° C., ≤about 500° C., or ≤about 400° C. These compositions, as herein described, comprise manganese, with in some embodiments sodium (or another alkali metal) and tungsten, with or without lanthanum or other rare earth elements, each in the form of an oxide, mixed oxide, hydroxide, carbonate, oxycarbonate and/or a salt. The disclosed technology further regards novel processes of oxidative dehydrogenation of methane (2 molecules), ethane (1 molecule), or mixtures thereof, to produce ethylene, ethane, propylene, propane, and other higher hydrocarbons and derivatives thereof as, for example, the stochiometric reactions $2CH_4+O_2 \rightarrow C_2H_4+2H_2O$ and $3CH_4+3/2\ O_2 \rightarrow C_3H_6+3H_2O$.

BACKGROUND OF THE INVENTION

Most research on oxidative coupling of methane (OCM) and other oxidative dehydrogenation reactions to produce ethylene, ethane, propylene and propane has been carried out at temperatures of 750-850° C. and higher, at near atmospheric pressures, since the original work in 1982 as reflected in "*Synthesis of Ethylene via Oxidative Coupling of Methane*", G. E. Keller and M. M. Bhasin, *Journal of Catalysis* Vol 73, pp. 9-19 (1982).

Importantly, all catalysts reported in the applicable literature are not stable for long periods of time (more than a week or so, at higher temperatures), and therefore lose activity. Stable catalyst performance is critical to the commercial viability of any OCM or oxidative dehydrogenation process.

Furthermore, relatively little work has been done using inert diluents like water, carbon dioxide, and nitrogen, to obtain higher conversion, higher selectivity and hence higher yields (≥about 20-30%).

In addition, studies indicate severe penalties of 3-8% loss in $C_2$-selectivity (and corresponding reductions in yields) per 1 atm when pressure is increased from 1 to 7.5 atm. See "*The Effect of Total Pressure on the Oxidative Coupling of Methane Reaction under Cofeed Conditions*", M. Pinabiau Carlier, et. al., *Natural Gas Conversion*, pp. 183-190 (1991); "*Effect of Pressure on the Oxidative Coupling Reaction of Methane,*" A. Ekstrom, R. Regtop, and S. Bhargava, *Applied Catalysis*, Vol. 62, pp. 253-269 (1990).

An in-depth review of methane conversion conducted in 1995 emphasized the challenges of operating at high pressure of about 10 atm (150 psig). See "*Methane and Alkane Conversion Chemistry,*" M. M. Bhasin and K. D. Campbell, editors M. M. Bhasin and D. W. Slocum, Plenum Press, NY, 1995. The main exceptions are the work done by Union Carbide, at high pressures (10-20 atm) and lower temperatures of about 500° C., in two patents issued in 2002 and 2003. See R. D. Cantrell, A. Ghenciu, K. D. Campbell, D. M. Minahan, M. M. Bhasin, A. D. Westwood, K. A. Nielsen, U.S. Pat. No. 6,403,523, Jun. 11, 2002 and 6,576,803, Jun. 10, 2003. These patents describe the prior art in detail and are incorporated herein by this reference.

Critical importance of the need for high pressures 4-9 atm, is also highlighted in two recent publications. "*High-pressure oxidative coupling of methane on alkali metal catalyst—Microkinetic analysis and operando thermal visualization*", Yuhang Yu, et. al. J. Catalysts, 432 (2024) 115414; "*Mn—Na₂WO₄/SiO₂-Tridymite with improved stability and selectivity for high-pressure oxidative coupling of methane*", Yuhang Yu, et. al., *Chemical Engineering Journal*, 500 (2024) 156938; see, also, "*Natural Gas Conversion to Value Added Chemicals*", H. R. Godini, M. M Bhasin and F. Gallucci, Chapter 5 in CRC Press, 2021, Edited by J. Hu and D. Shekhawat. One of the first two publications has shown smaller decrease in selectivity at 9 atm, but this catalyst has to be operated ≥750° C. for relatively short durations of about 10 days. Typical loss in selectivity from 1-9 bar was 2.8% selectivity per each bar increase in pressure. Some improvement in stability for 100 hours was obtained with another catalyst in the second reference, Mn (2 wt %)-Na₂WO₄ (5 wt %) on SiO₂-Tridymite operating at 775° C.

Therefore, all reported work has been a surface-initiated gas phase coupling of methane through methyl radicals, with the undesirable combustion products, CO and $CO_2$.

Finally, there has been an established belief in the prior art that the sum of conversion and selectivity percentages in oxidative dehydrogenation reactions cannot exceed 100%, also popularly known as the "Rule of 100". The vast majority of the reported work has reported yields of ≤30%, frequently ≤25%, and typically <10%, at reaction temperatures in the range of 750-800+° C. and at 1 atm.

Hence, oxidative dehydrogenation of methane and ethane at temperatures ≤about 700° C., ≤about 650° C., ≤about 600° C., ≤about 500° C., or ≤about 400° C., and pressures of about 5-10 atm or higher, are necessary to obtain high selectivity of ≥about 40%, ≥about 60%, ≥about 70%, ≥about 80%, or ≥about 90%, and at high conversions of ≥about 15%, ≥about 20%, ≥about 30%, ≥about 40%; or ≥about 50%; thereby resulting in yields ≥about 20%, ≥about 30%, ≥about 40% or ≥about 50%. Such high yields have not been reported to date. For commercial success, the catalyst and its performance should remain stable for ≥about 15 days, ≥about 35 days, ≥about 100 days, ≥about 200 days, or ≥about 1 year.

GENERAL DESCRIPTION OF THE INVENTION

The disclosed technology provides novel, stable catalyst compositions including manganese, and in embodiments sodium and tungsten, with or without lanthanum oxide, which have demonstrated remarkable stability at higher pressures and lower temperatures. Another novel aspect of the catalyst compositions of the disclosed technology is that the performance, particularly the selectivity to desired products (ethylene/ethane and propylene/propane), increases at higher space velocity (flow rates). This aspect of the invention provides additional benefit by reducing the size of the reactor for the catalytic conversion of methane into ethylene/ethane and propylene/propane.

In an embodiment, a catalyst is provided for the oxidative dehydrogenation of methane and/or ethane, the catalyst comprising manganese, wherein the catalyst when used for the oxidative dehydrogenation of the lower hydrocarbon at a pressure ≥about 5 atm, at reaction site temperatures (measured at the reactor wall)≤about 600° C., and employing gas hourly space velocities (GHSV) ≥about 1,000 h⁻¹, has a conversion of ≥about 10% into at least one higher hydrocarbon, its derivatives and amines, and a selectivity for $C_2$ or $C_3$, or both, of ≥40%, for a period of ≥15 days.

In this and other embodiments, a catalytic process for the oxidative dehydrogenation of methane and/or ethane is provided, the process occurring in the presence of a catalyst comprising manganese, wherein the process operates at pressures ≥about 5 atm, at reaction site temperatures (measured at the reactor wall)≤about 600° C., and utilizes GHSV≥about 5,000 h$^{-1}$, wherein the process has a conversion of ≥about 10% into at least one higher hydrocarbon, its derivatives and amines, and a selectivity for C$_2$ or C$_3$, or both, of ≥about 40%, for a period of ≥about 15 days.

DETAILED DESCRIPTION OF THE INVENTION

Figure 1:
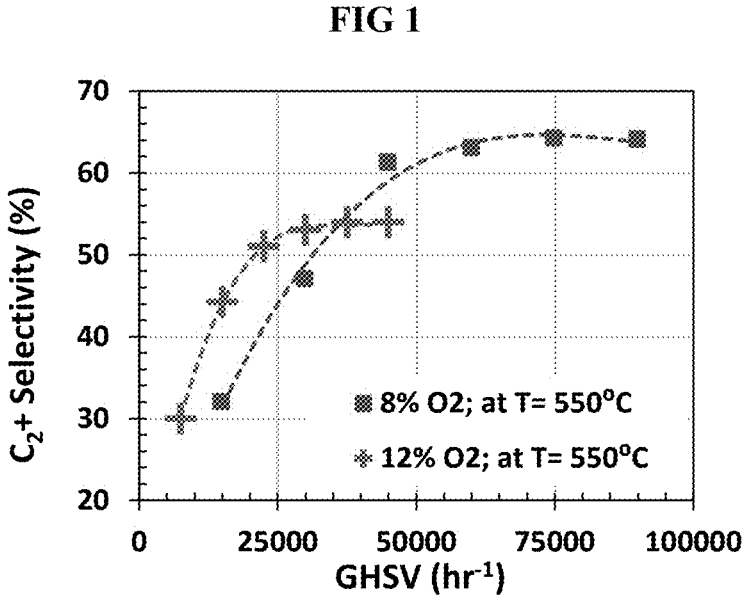
FIG. 1 is a plot showing Example 1, Type I catalyst C$_2^+$ selectivity at different feed O$_2$ with CH$_4$ fixed at 78%/Bal N$_2$.

The disclosed novel catalyst compositions comprise at least manganese, and optionally one or more cocatalysts selected from the group consisting of: tungsten (W), and rare earth metal oxides or oxycarbonates with the rare earth element selected from the subgroup consisting of: lanthanum (La), cerium (Ce), praseodymium (Pr), neodymium (Nd), samarium (Sm), europium (Eu), gadolinium (Gd), thorium (Th), dysprosium (Dy), holmium (Ho), erbium (Er), and thulium (Tm); and optionally one or more promoters selected from the group consisting of: sodium (Na), lithium (Li), potassium (K), rubidium (Rb), and cesium (Cs), to impregnate the catalyst on the support. Each of the foregoing elements may be in the form of an oxide, mixed oxide, hydroxide, carbonate, oxycarbonate and/or a salt.

The novel catalyst may be deposited on an inert catalyst support, such as an alpha-alumina or silicon carbide support, or a support selected from refractory oxides, carbides, oxycarbides, nitrides, or oxynitrides, or a zirconia support.

In embodiments, manganese may be present in composition including the support as ≥about: 1% w/w, 5% w/w, 10% w/w, 20% w/w, 50% w/w, or higher. In these embodiments, additional cocatalysts and promoters may optionally be included in the composition, including tungsten (between about 3-25% w/w, or about 10-25% w/w), sodium (between about 2-15% w/w, or about 10-15% w/w), and lanthanum (between about 1-70% w/w). Each of the foregoing elements may be in the form of an oxide, mixed oxide, hydroxide, carbonate, oxycarbonate and/or a salt. For purposes of this disclosure, the term "about" is defined to mean+/−five percent (5%) of a stated value.

Using this novel catalyst, a novel method of oxidative dehydrogenation of methane or ethane, or both, is provided, with a source of oxygen. When methane is coupled by oxidative dehydrogenation, ethylene, propylene and water are produced according to the following net reactions.

$$2CH_4+O_2 \rightarrow C_2H_4+2H_2O$$

$$3CH_4+3/2O_2 \rightarrow C_3H_6+3H_2O$$

Ethane and propane and water are produced according to the following net reactions:

$$2CH_4+\frac{1}{2}O_2 \rightarrow C_2H_6+H_2O$$

$$3CH_4+O_2 \rightarrow C_3H_8+2H_2O$$

The methane and higher hydrocarbons can also undergo combustion to produce carbon monoxide, carbon dioxide, and water.

$$CH_4+2O_2 \rightarrow CO_2+2H_2O$$

$$CH_4+3/2O_2 \rightarrow CO+2H_2O$$

In addition, secondary oxidative dehydrogenation reactions producing ethylene, propylene, and propane may occur such as the following:

$$C_2H_6+\frac{1}{2}O_2 \rightarrow C_2H_4+H_2O$$

$$C_3H_8+\frac{1}{2}O_2 \rightarrow C_3H_6+H_2O$$

$$CH_4+C_2H_6+\frac{1}{2}O_2 \rightarrow C_3H_8+H_2O$$

Further reactions may produce derivatives of ethylene or propylene, or derivatives and corresponding amines of the foregoing, including the derivatives of ethylene oxide and ethylene glycol, and their derivatives.

The oxidative dehydrogenation methods of the disclosed technology include contacting the novel catalyst compositions as herein disclosed, in the presence of oxygen, with feedstock comprising natural gas, methane, ethane, or mixtures thereof, wherein any C$_3$ hydrocarbons, C$_4$ hydrocarbons, and higher hydrocarbons, and sulfur and sulfur compounds have been removed. Importantly, the feedstock contacts the catalyst: (a) at operating temperatures (at the reaction site)≤about 700° C., ≤about 650° C., ≤about 600° C., ≤about 500° C., or ≤about 400° C.; (b) at operating pressures ≥about 5 atm, ≥10 atm, or ≥20 atm; and/or (c) wherein the volumetric flow rate of the feedstock per unit volume of catalyst per hour (gas hourly space velocity, or GHSV, measured at 1 atm) may be between about 1,000-

100,000 h$^{-1}$, or ≥about 1,000 h$^{-1}$, ≥about 5,000 h$^{-1}$, ≥about 10,000 h$^{-1}$, ≥about 15,000 h$^{-1}$, or ≥about 20,000 h$^{-1}$, ≥about 30,000 h$^{-1}$, ≥about 45,000 h$^{-1}$, ≥about 50,000 h$^{-1}$, ≥about 60,000 h$^{-1}$, or ≥about 100,000 h$^{-1}$. Herein, when referenced the operating temperature is measured at the outside reactor wall, acknowledging that the oxidative dehydrogenation process is an exothermic reaction, generating heat at the reaction site. Notably, much of the prior art expressly or presumably references the temperature at the inlet to the catalyst bed, not considering the heat generated by the reaction.

Using this oxidative dehydrogenation method and the disclosed catalyst, the reaction may achieve high conversion of methane into the desired $C_2$ and $C_3$ products (e.g., ethane ethylene, propane, propylene) or other higher hydrocarbons, ≥about 15%, ≥about 20%, ≥about 30%, ≥about 40%, ≥about 50%, or ≥about 70%; and high selectivity of $C_2$ and $C_3$ hydrocarbons of ≥about 40%, ≥about 60%, ≥about 70%, ≥about 80%, or ≥about 90%. For purposes of this disclosure, "conversion" means the percentage of methane converted to another product (e.g., ethane, ethylene, propane, propylene, carbon monoxide, etc.), and "selectivity" means the percentage of a desired product (e.g., $C_2$ and $C_3$ hydrocarbons) relative to total carbon products produced. Further, the stability of the catalyst is defined as the length of time a catalyst will maintain its catalytic performance without a decrease of ≥about 20%, ≥about 10%, ≥about 5%, ≥about 2%, or ≥about 1%, in $C_2$ or $C_3$ (or both) yield, $C_2$ or $C_3$ (or both) selectivity or methane conversion. In some embodiments, the disclosed catalysts have or may have stability under conditions required for the oxidative dehydrogenation reaction of ≥about 15 days, ≥about 35 days, ≥about 100 days, ≥about 200 days, or ≥about 1 year, without needing to rejuvenate or regenerate the catalyst with a feed of nitrogen or oxygen, or any other rejuvenation or regeneration process known in the art.

In the oxidative dehydrogenation method of the disclosed technology using the disclosed novel catalyst, various diluents can be employed. For example, steam may be provided as a diluent, which may be easily removed post-reaction. Further, other known diluents such as carbon dioxide, nitrogen, argon or other non-reactive gases, may be used alone, in combination, or in mixture with steam, to achieve high selectivity at high conversions as hereinabove described.

This oxidative dehydrogenation method and the disclosed novel catalyst is particularly useful with natural gas, which comprises both methane and smaller amounts of ethane, and sometimes propane. Following removal of $C_3$, $C_4$ and higher hydrocarbons (also called liquid hydrocarbons) and sulfur impurities from the natural gas, the remaining methane and ethane (and propane) mixture may be supplied as feedstock to the catalyst in the reaction chamber, under the conditions herein set forth, to produce the valuable higher carbon products.

The disclosed method and catalyst offer improved economics, wherein for example: (a) the higher GHSV significantly increases the volume of valuable higher carbon products produced by a reactor, and thereby allows for a significantly reduced reactor size; (b) the high selectivity at high conversions achieved by the disclosed technology in the presence of easy to separate water/steam and/or carbon dioxide diluents, drive process simplicity (and thereby reduce cost); and (c) the lower reaction temperatures provide a far simpler reactor design utilizing more traditional tube and shell heat exchanger type designs, among other benefits.

For these and other reasons, the catalysts and oxidative dehydrogenation methods herein described can be useful and provide economic synergies in numerous industrial operations, including without limitation vertical integration at the oil wellhead, producing ethylene, propylene, ethane and propane.

EXAMPLES OF CATALYST PREPARATION

Two embodiments of the novel catalyst compositions were prepared using well-known aqueous impregnation techniques from readily available water-soluble salts, as hereinafter described.

Example 1, Type I

This catalyst has a composition of W/Mn/Na/La=1/2.875/1.78/38 (atomic ratio), with the active catalytic components deposited on high purity lanthanum (III) oxide ($La_2O_3$) powder with a purity of 99.9% from Fisher Scientific Chemicals Inc. The active catalytic components from the same supplier are: (i) manganese(II) nitrate tetrahydrate (98%), (ii) ammonium tungsten oxide hydrate, and (iii) sodium nitrate (99%). The catalyst was prepared by: (a) heating 500 ml of deionized water in a beaker to 50° C.; (b) dissolving in the water 3.4 grams of ammonium tungsten oxide hydrate, 9.9 grams of manganese(II) nitrate tetrahydrate (98%), and 2.1 grams of sodium nitrate; (c) constantly stirring and heating on a stirring hot plate the dissolved salts for 15 minutes, allowing them to come to equilibrium; (d) adding and continuously stirring 86 grams of lanthanum (III) oxide (99.9%) to the beaker content; (e) raising the temperature of the bulk solution to about 80° C., and stirring until much of the water has evaporated, leaving a viscous paste in the bottom of the beaker; (f) transferring the contents of the beaker to alumina crucibles and loaded into an air-fed calcination furnace and held overnight at 100° C. to evaporate any remaining moisture; and (g) increasing the furnace temperature to 800° C. for 6 hours to calcine the material.

Example 2, Type II

This catalyst has a composition of W/Mn/Na=1/2.875/1.78 (atomic ratio), with the active catalytic components deposited on porous alpha-alumina pellets. The active catalytic components were the same as those disclosed in Type 1, above. The catalyst was prepared by: (a) heating 500 ml of deionized water in a beaker to 50° C.; (b) dissolving in the water 6.8 grams of ammonium tungsten oxide hydrate, 19.8 grams of manganese(II) nitrate tetrahydrate (98%), and 4.2 grams of sodium nitrate; (c) constantly stirring and heating on a stirring hot plate the dissolved salts for 15 minutes, allowing them to come to equilibrium; (d) adding and continuously stirring 86 grams of alpha alumina pellets SA5162 (Saint-Gobain Corporation), having a $N_2$ surface area of 0.72 m$^2$/g and pore volume of 0.53 cc/g, with trimodal pore size distribution; (e) raising the temperature of the bulk solution to about 80° C., and stirring until the heated salt solution was impregnated into the alumina supports: (f) transferring the contents of the beaker to alumina crucibles and loaded into an air-fed calcination furnace and held overnight at 100° C. to evaporate any remaining moisture; and (g) increasing the furnace temperature to 800° C. for 6 hours to calcine the material.

US 12,612,345 B1

7

Catalyst Evaluations in Microreactor

Catalyst evaluations were done in three parallel stainless steel reactor test systems. Extensive background activity testing was done to minimize the gas phases and the reactor wall activity for methane combustion and/or methane coupling; because this background activity is dependent on temperatures, the contribution is relatively small for the disclosed catalysts.

The reactor used was an assembly of a 0.188" inner diameter and 0.313" outer diameter alumina tube lined inside a 0.319" inner diameter 316 stainless steel tube. This 18" long alumina-lined stainless steel tubular reactor assembly has proven to be somewhat inert and structurally stable for oxidative dehydrogenation reactions. The reactor was attached to a 12" length single zone heating furnace with an approximate 5" length isothermal zone where the catalyst bed is situated, and the furnace temperature controlled with a thermocouple attached to the reactor wall. The temperatures specified in these examples refer to reactor temperatures, which correspond to the furnace setpoint temperature as measured by a thermocouple in contact with the reactor wall.

The reactor was charged with catalyst sandwiched between beds of silicon carbide, wherein the catalysts had been screened to a desired particle size of 354-180 microns. The feed gases were fed into the reactor using a digital mass flow controller (MFC), and the products gases were analyzed using online gas chromatography. In the catalyst testing experiments, unless indicated otherwise, nitrogen was used as a diluent gas with methane and oxygen as the main feedstock. The loaded catalysts were purged overnight at 500° C. and atmospheric pressure under nitrogen before bringing online.

Example 3—Using Example 1, Type I Catalyst, W/Mn/Na/La=1/2.875/1.78/38)

The Type I catalyst was loaded in the alumina-lined reactor and after standard nitrogen purge was pressurized to 150 psig (10 atm) by a feed gas composition of 12% $O_2$, 78% $CH_4$/Bal $N_2$ at a fixed reactor temperature of 550° C. The gas flowrate was set at 253 SCCM and a GHSV of 15,000 h$^{-1}$ and held until steady state performance was achieved. Subsequently the gas flowrate and GHSV was raised incrementally over three hours to 759 SCCM and 45,000 h$^{-1}$, respectively. In one configuration, the feed $O_2$ was then decreased to 8%. In both configurations the GHSV was increased to 90,000 h$^{-1}$.

Figure 2:
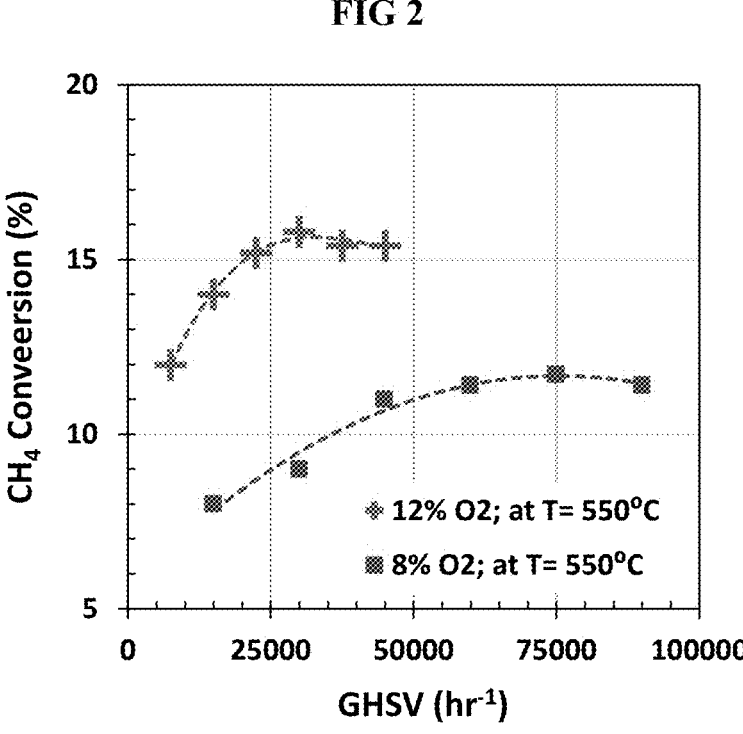
FIG. 2 is a plot showing Example 1, Type I catalyst CH$_4$ conversion at different feed O$_2$ with CH$_4$ fixed at 78%/Bal N$_2$.

The results are shown in FIGS. 1 and 2. The catalyst showed an increase in performance (selectivity and $CH_4$ conversion) with flowrate in both configurations, although this performance increase flattens out at some point even while increasing the flowrate. The selectivity and conversion will increase as the catalyst and the process conditions are optimized, using methods known in the art.

Figure 3:
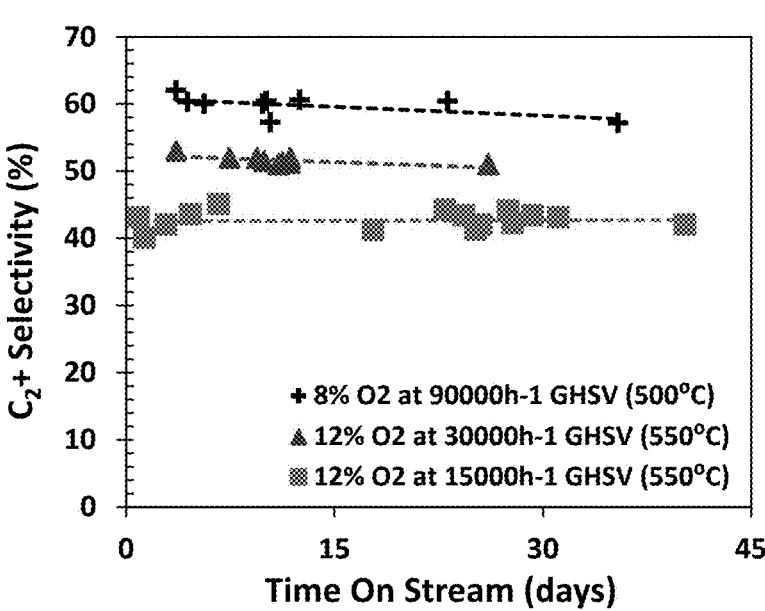
FIG. 3 is a plot showing Example 1, Type I catalyst C$_2^+$ selectivity plot for stability test at a fixed Feed=12% O$_2$, 78% CH$_4$, and Bal N$_2$, or 8% O$_2$, 78% CH$_4$, and Bal N$_2$.
Figure 4:
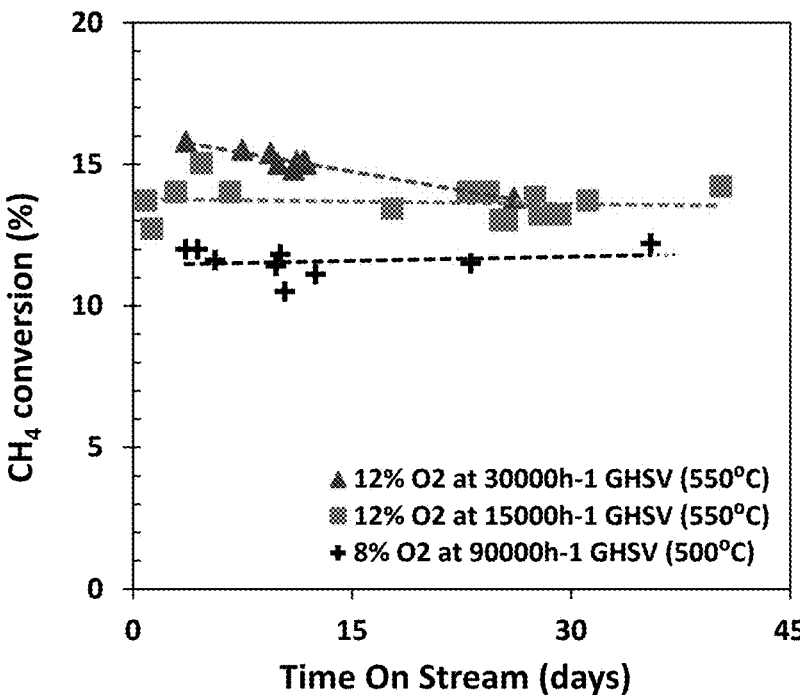
FIG. 4 is a graph showing Example 1, Type I catalyst CH$_4$ conversion plot for stability test at a fixed Feed=12% O$_2$, 78% CH$_4$, and Bal N$_2$, or 8% O$_2$, 78% CH$_4$, and Bal N$_2$.

As shown in FIGS. 3 and 4, using the feed $O_2$ at 8% or 12%, at different flowrates (15,000 h$^{-1}$, 30,000 h$^{-1}$ and 90,000 h$^{-1}$), this catalyst performance shows decent stability behavior over a run period of 40 days.

Example 4—Using Example 2, Type II Catalyst, W/Mn/Na=1/2.875/1.78 on α-Al$_2$O$_3$ The Type-II catalyst was loaded in the alumina-lined reactor and after standard nitrogen purge was pressurized to 150 psig by a feed gas composition of 12% $O_2$, 78% $CH_4$/Bal $N_2$ at a fixed reactor temperature of 650° C. The gas flowrate was set at 253 SCCM and a GHSV of 15,000 h$^{-1}$ and held until there is steady state performance. Subsequently the gas flowrate and GHSV were raised incrementally up to 759 SCCM and 45,000 h$^{-1}$, respectively. In one configuration, the feed $O_2$ was decreased to 8%. In both configurations the GHSV was increased to 30,000 h$^{-1}$, and then to 90,000 h$^{-1}$.

Figure 5:
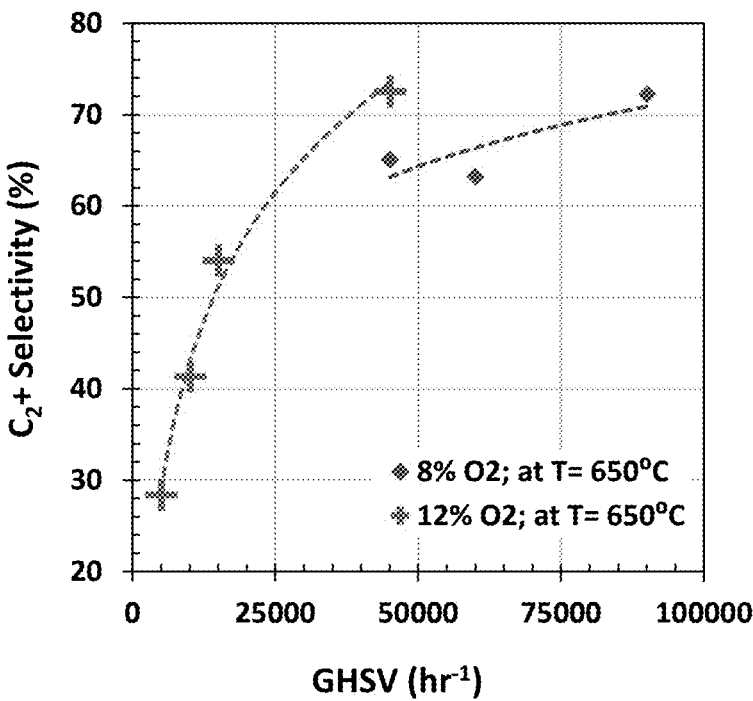
FIG. 5 is a graph showing Example 1, Type I catalyst C$_2^+$+ selectivity plot at different feed O$_2$ with CH$_4$ fixed at 78%/Bal N$_2$.
Figure 6:
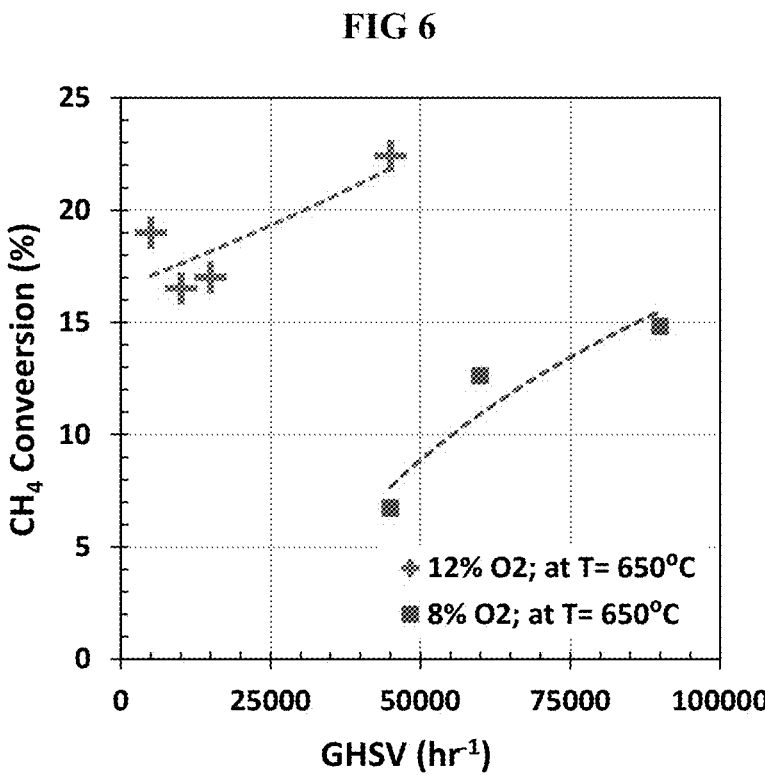
FIG. 6 is a graph showing Example 1, Type I catalyst CH$_4$ conversion plot at different feed O$_2$ with CH$_4$ fixed at 78%/Bal N$_2$.

The results were shown in FIGS. 5 and 6. The catalyst showed an increase in performance (selectivity and $CH_4$ conversion) with flowrate in both configurations, although this performance increase flattens out at some point while increasing the flowrate. The selectivity and conversion will increase as the catalyst and the process conditions are optimized, using optimization methods known in the art.

Figure 7:
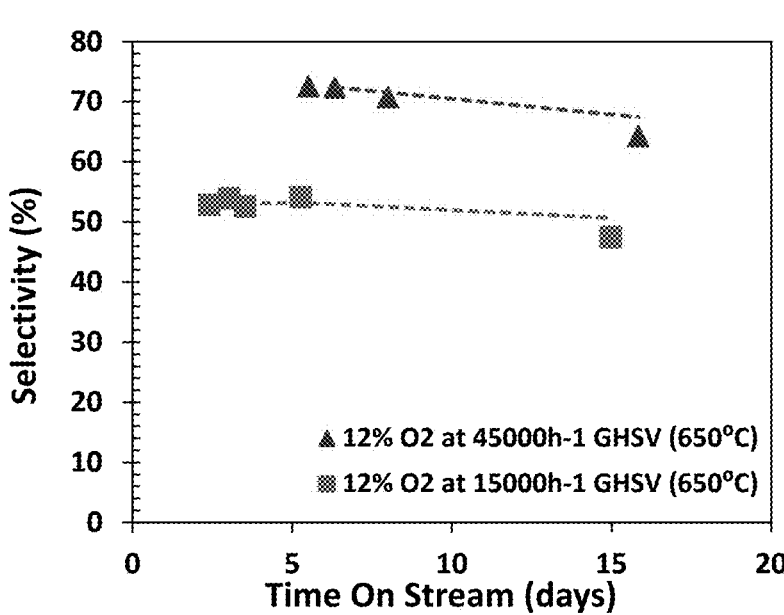
FIG. 7 is a graph showing Example 2, Type II catalyst C$_2^+$ selectivity plot for stability test at a fixed Feed=12% O$_2$, 78% CH$_4$, and Bal N$_2$.
Figure 8:
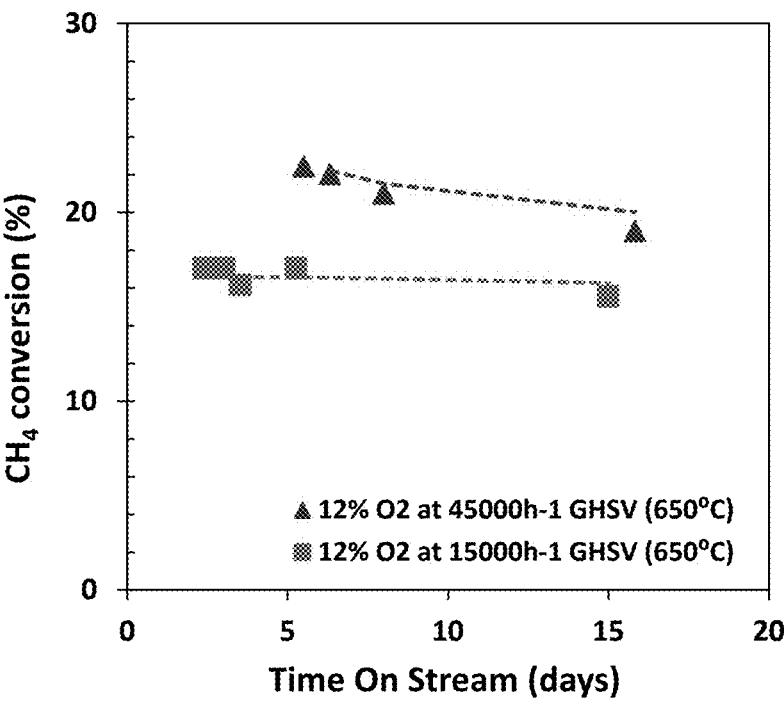
FIG. 8 is a graph showing Example 2, Type II catalyst CH$_4$ conversion plot for stability test at a fixed Feed=12% O$_2$, 78% CH$_4$, and Bal N$_2$.

As shown in FIGS. 7 and 8, using the feed $O_2$ at 12%, at two different flow rates (15,000 h$^{-1}$ and 45,000 h$^{-1}$), this catalyst performance shows decent stability behavior over a run period of 15 days.

Example 5—Effect of Steam Diluent Using Example 1, Type I Catalyst

Figure 9:
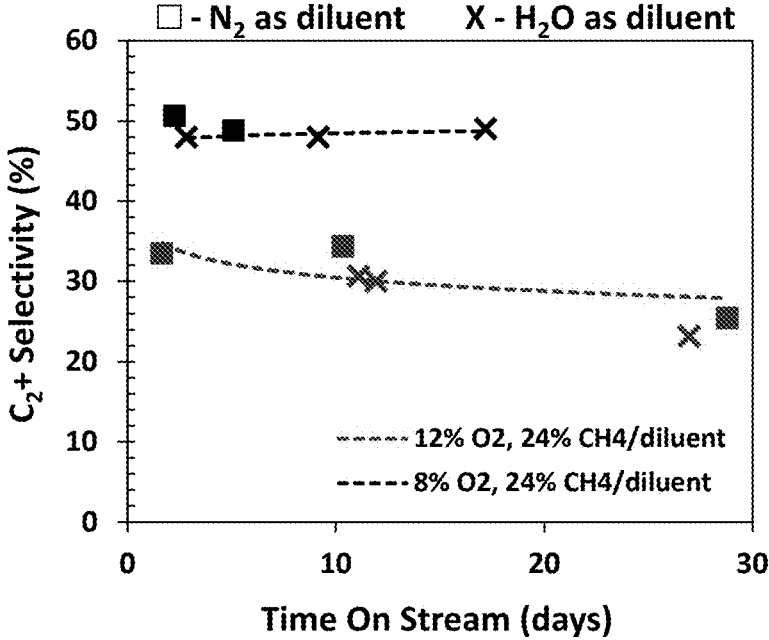
FIG. 9 is a graph showing Example 1, Type I catalyst C$_2^+$ selectivity plot for stability test at a fixed Feed=78% CH$_4$, and Bal N$_2$ or H$_2$O.
Figure 10:
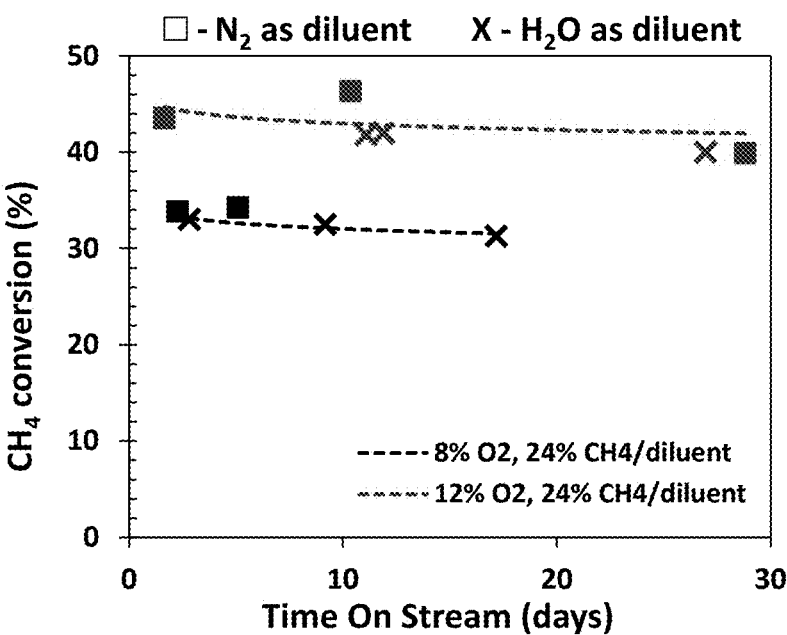
FIG. 10 is a graph showing Example 1, Type I catalyst CH$_4$ conversion plot for stability test at a fixed Feed=78% CH$_4$, and Bal N$_2$ or H$_2$O.

As described earlier, steam as diluent (in place of $N_2$) is highly desirable for superior economics, primarily due to the ease of separation. Catalyst evaluations were carried out to determine the effect of steam ($H_2O$) on the catalyst performance using the catalyst of Example 1, Type I. Various conditions evaluated with $N_2$ and steam are listed in Table 1 below, with the feed as in Example 3, and the furnace temperature at 550° C. Key performance metrics show only a slight variation in activity/selectivity with steam diluent. These results are very desirable since switching from $N_2$ to steam did not inhibit the reaction and in fact it still maintained a nearly equivalent performance. Further, as shown in FIGS. 9 and 10, this catalyst remained stable at selected conditions with the diluent interchanging between nitrogen and steam.

TABLE 1

| Condition | $O_2$ | $CH_4$ | Diluent | $O^2$ conv. % | $CH_4$ conv. % | $C_2$+ sel. % | $C_2$+ yield. % |
|---|---|---|---|---|---|---|---|
| 1 | 10 | 16 | $N_2$ | 91 | 55 | 38 | 21 |
|  |  |  | Steam | 92 | 49 | 40 | 20 |
| 2 | 8 |  | $N_2$ | 88 | 46 | 43 | 20 |
|  |  |  | Steam | 97 | 41 | 44 | 18 |
| 3 | 10 | 24 | $N_2$ | 91 | 42 | 43 | 18 |
|  |  |  | Steam | 96 | 40 | 43 | 17 |
| 4 | 8 |  | $N_2$ | 91 | 34 | 51 | 17 |
|  |  |  | Steam | 98 | 33 | 46 | 15 |
| 5 | 12 |  | $N_2$ | 96 | 46 | 34 | 16 |
|  |  |  | Steam | 98 | 42 | 31 | 13 |

Example 6 (Comparative)

One of the best prior art catalysts, $Mn$—$Na_2$ $WO_4$/$SiO_2$, which under tests has proven to maintain reasonable stability over 1,000 hours time on stream (under 1 bar pressure, 750°–875° C. operations) was evaluated in the same reactor system as described above in Examples 3-5. See, "*Reaction of engineering of oxidative coupling of methane. Experimental observations and analysis of the impacts of operating parameters.*", M. Kim, S. Arndt, M. Yildiz, R. Schomäcker, O. Göcke, G. Wozny and H. R. Godini, *Chemical Engineering Research and Design*, Vol. 172, (2021) pp. 84-98. To make absolutely certain that this catalyst is indeed the same catalyst as reported in the the literature, the applicant obtained the catalyst from the inventor H. R. Godini. The catalyst was loaded in the alumina-lined reactor and after standard nitrogen purge was pressurized to 150 psig by a feed gas composition of 12% $O_2$, 78% $CH_4$/Bal $N_2$ with gas flowrate set at 253 SCCM and a GHSV of 15,000 $h^{-1}$. Evaluation started at a furnace temperature of 550° C. until steady state performance was achieved, and subsequently increased incrementally to 750° C. Conversion and selectivity at 150 psig and 1 atm, respectively, are shown in FIGS. 11*a* and 11*b*.

Figure 11A:
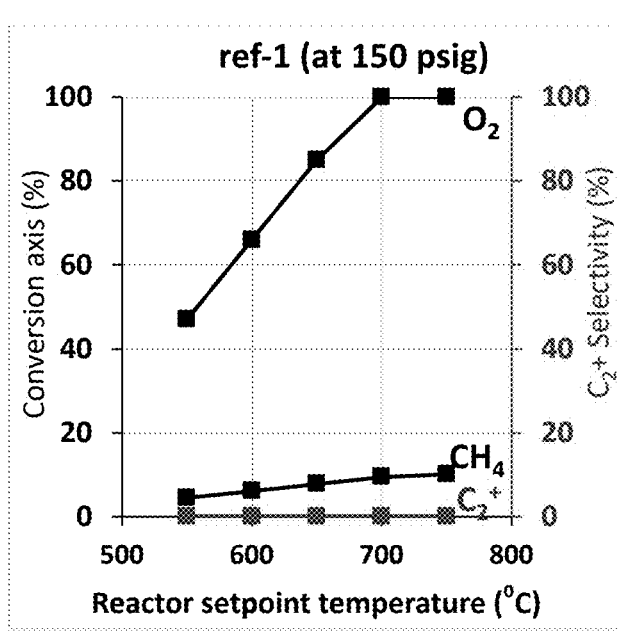
FIGS. 11a and 11b are graphs showing performance plot w.r.t reaction temperature for example 6 (150 psig and 1 atm, respectively). Evaluation at a fixed feed condition of 12% O$_2$, 78% CH$_4$ and balance N$_2$. Reaction GHSV=15000 h$^{-1}$.
Figure 11B:
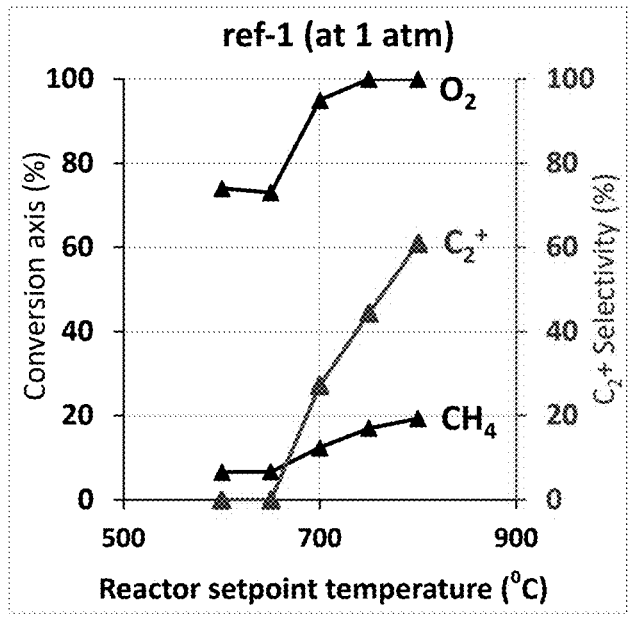
Figure 12A:
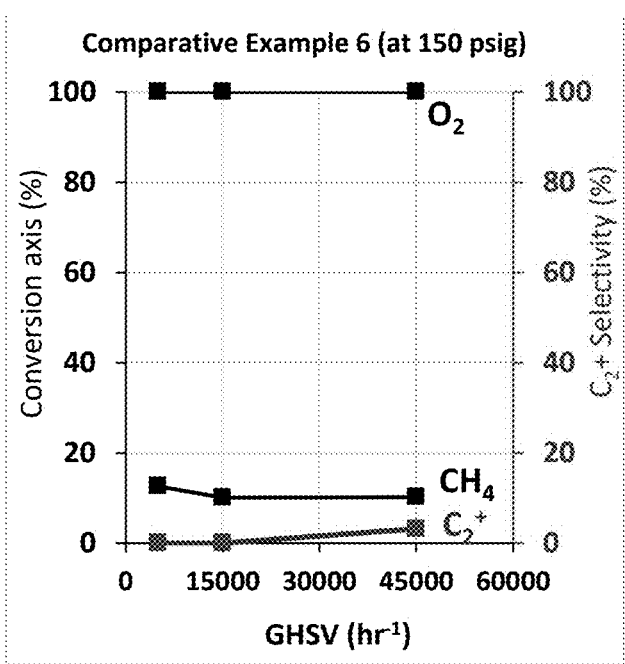
FIGS. 12a and 12b are graphs showing performance plot w.r.t reaction GHSV for a certain prior art catalyst, as referenced in Example 6 below. Evaluation at a fixed feed condition of 12% O$_2$, 78% CH$_4$ and balance N$_2$. Reaction temperature is at 750° C.
Figure 12B:
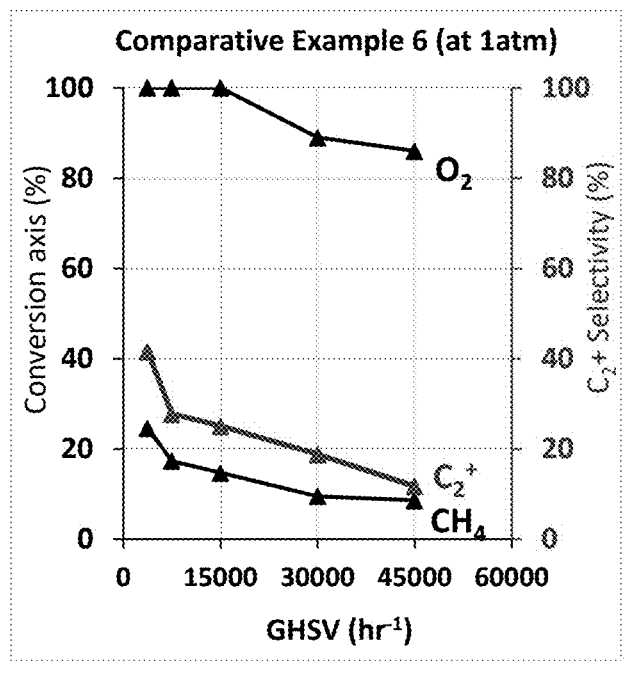

As shown in FIGS. 11*a* and 11*b*, this catalyst (while exhibiting good oxygen conversion and high selectivity at 1 atm pressure, at high temperatures), has low conversion and low selectivity at 150 psig (only producing combustion products), especially at lower temperatures of 450° C. to 600° C., even though the $O_2$ is completely reacted at 700° C. and above. Further, as shown in FIGS. 12*a* and 12*b*, this catalyst performs poorly at higher GHSV, regardless of pressure.

The invention claimed is:

1. A catalytic process for the oxidative dehydrogenation of methane or methane with ethane, the process occurring in the presence of a catalyst comprising manganese in the form of an oxide, mixed oxide, hydroxide, carbonate, oxycarbonate or a salt, or a combination thereof, wherein the process operates at pressures above about 5 atm, at reaction temperatures below about 600° C., and utilizes gas hourly space velocities above about 5,000 $h^{-1}$, wherein the process has a conversion of at least 10% into at least one higher hydrocarbon, its derivatives and amines, and a selectivity for $C_2$ or $C_3$, or both, of at least about 40%, for a period of at least 15 days without requiring regeneration.

2. The process of claim 1, wherein the process is carried out at pressures above about 10 atm.

3. The process of claim 1, wherein the process is carried out at temperatures below about 500° C.

4. The process of claim 1, further comprising one or more alkali metals in the form of an oxide, mixed oxide, hydroxide, carbonate, oxycarbonate or a salt, or a combination thereof, selected from the group consisting of lithium, sodium, potassium, rubidium, cesium, and optionally a rare earth metal oxide.

5. The process of claim 4, wherein the rare earth metal oxide is lanthanum oxide, and the lanthanum oxide comprises between 1% and 70% by weight of the catalyst.

6. The process of claim 1, wherein the gas hourly space velocities are above about 10,000 $h^{-1}$.

7. The process of claim 1, wherein the catalyst comprises manganese in combination with tungsten and sodium.

8. The process of claim 7, wherein the catalyst is deposited on a lanthanum oxide support.

9. The process of claim 1, wherein the reaction temperature is measured at the outside of the reactor wall.

10. The process of claim 1, wherein the selectivity for $C_2$ or $C_3$ increases with increasing gas hourly space velocity.

* * * * *